(12) United States Patent
Laing et al.

(10) Patent No.: US 6,569,628 B2
(45) Date of Patent: *May 27, 2003

(54) SCREEN EMPLOYING FLUORESCENCE ANISOTROPY TO IDENTIFY COMPOUNDS WITH AFFINITY FOR NUCLEIC ACIDS

(75) Inventors: Lance G. Laing, Belmont, MA (US); Jaime E. Arenas, Lexington, MA (US); Sharon T. Cload, Cambridge, MA (US); James W. Lillie, Natick, MA (US); Andrew A. Pakula, Lexington, MA (US)

(73) Assignee: Anadys Pharmaceuticals, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/961,008

(22) Filed: Sep. 20, 2001

(65) Prior Publication Data

US 2002/0031778 A1 Mar. 14, 2002

Related U.S. Application Data

(63) Continuation of application No. 09/060,449, filed on Mar. 5, 1998, now Pat. No. 6,331,392.
(60) Provisional application No. 60/039,911, filed on Mar. 5, 1997.

(51) Int. Cl.[7] .......................... C12Q 1/68; G01N 33/53
(52) U.S. Cl. .............................. 435/6; 435/7.1
(58) Field of Search ............... 435/6, 7.1, 91.2; 536/22.1, 23.1

(56) References Cited

U.S. PATENT DOCUMENTS

| 4,859,609 A | 8/1989 | Dull et al. |
| 5,118,801 A | 6/1992 | Lizardi et al. |
| 5,200,504 A | 4/1993 | Ghadiri |
| 5,270,163 A | 12/1993 | Gold et al. |

(List continued on next page.)

FOREIGN PATENT DOCUMENTS

| EP | 0 613 007 A2 | 8/1994 |
| WO | WO 92/03542 | 5/1992 |
| WO | WO 93/14781 | 5/1993 |

(List continued on next page.)

OTHER PUBLICATIONS

Calcutt et al., Gene, 137(1):77–83 (1993).
Pesce et al., Nucleic Acid Research, 22(4): 656–661 (1994).
Markovitz et al., Analytical Biochemistry, 94:259–264 (1970).
Rye et al, Nucleic Acid Research, 20:2803–2812 (1992).
Airas, Biochemistry, 33:7193 (1994).
Friguet et al., Protein Structure: A Practical Approach, Creighton, Ed., IRL Press (Oxford 1989).
Volkins et al., Proceedings of the Ninth International Biotechnology Symposium and Exposition, American Chemical Society, 1992, cover pages and pp. 299–302.
Fercht, Curr. Opinion in Struc. Biol. 7:3 (1997).
Schellman, Biopolymers, 15:999–1000 (1976).
Tanigaki, Nobuyuki (Citation Unknown) pp. 577–690 (1993).
Weber et al., J. Am. Chem. Soc., 16:2716 (1994).
Burke et al., Biochemistry, 32:6419–6426 (1993).
Volkin et al., Archives of Biochemistry and Biophysics, 300:31–41 (1993).
Hu et al., Biochemistry, 31:4876–82 (1991).
Copeland et al., Archives of Biochemistry and Biophysics, 289:53–61 (1991).
Dabora et al., J. Biol. Chem., 266:23637–40 (1991).
Pace, TIBS 15, Jan. 1990, 14–17.
Keating et al., Biochemistry, 27:5240–5 (1988).
Permyakov et al., Biophys. Chem., 32:37–42 (1988).
Allen and Wong, Arch. Biochim. Biophys., 249:137–147 (1986).
Busby and Ingham, Biochem. Biophys. Acta, 871:61–71 (1986).
Pace and Creighton, J. Mol. Biol., 188:477–486 (1986).
Schnarr and Maurizot, Biochim. Biophys. Acta, 871:61–71 (1986).
Klesov and Gerasimas, Biokhimiia, 44:1084–92 (1979).
Oobatake et al., J. Biochem., 86:65–70 (1979).
Blazyk and Lam, Biochemistry, 15:2843–8 (1976).
Doyle et al., Carbohydr. Res., 46:111–8 (1976).
DeFlora et al., Ital. J. Biochem., 24:147–61 (1975).
Takahasi, J. Biochim., 75:201–204 (1974).
Ranall, Science, 257:241–245 (1922).
Brandts et al., Biochemistry, 29:6927 (1990).
Parsell and Sauer, J. Biol. Chem., 264:7590–7595 (1989).
Pace and McGrath, J. Biol. Chem., 255:3862–3865 (1980).
Green et al., J. Biol. Chem., 266:21472 (1991).
Wagenhofer et al., Anal. Biochem., 175:422–432 (1988).
Cass–Finet et al., J. Mol. Biol., 229:873–889 (1988).
Kuwajima et al., Int. J. Peptide Protein Res., 27:18–27 (1986).
Lapadat and Spremulli, J. Biol. Chem., 24:5510–5514 (1989).
Feng and Sligar, Biochemistry, 35:10150–10155 (1991).
Tanigaki et al., Human Immunology, 36:119–127 (1993).

Primary Examiner—Kenneth R. Horlick
(74) Attorney, Agent, or Firm—David R Preston & Associates (57) ABSTRACT

The present invention provides methods for screening for bioactive compounds, in particular those that bind to RNA sequences involved in the pathogenesis of disease or in regulation of a physiological function. The methods involve assessing the stability and/or the conformation of an RNA target in the presence and absence of test ligands, and identifying as a ligand any test ligand that causes a measurable change in target RNA stability and/or conformation. In a preferred embodiment, the effect of a ligand on target RNA stability and/or conformation is assessed by measuring the fluorescence polarization of a fluorescently labeled probe.

9 Claims, 6 Drawing Sheets

U.S. PATENT DOCUMENTS

| | | |
|---|---|---|
| 5,306,619 A | 4/1994 | Edwards et al. |
| 5,312,921 A | 5/1994 | Glazer et al. |
| 5,325,295 A | 6/1994 | Fratantoni et al. |
| 5,348,941 A | 9/1994 | Middaugh et al. |
| 5,496,938 A | 3/1996 | Gold et al. |
| 5,506,097 A | 4/1996 | Potter et al. |
| 5,514,546 A | 5/1996 | Kool |
| 5,561,222 A | 10/1996 | Keene et al. |
| 5,567,588 A | 10/1996 | Gold et al. |
| 5,580,722 A | 12/1996 | Foulkes et al. |
| 5,585,277 A | 12/1996 | Bowie et al. |
| 5,679,285 A | 10/1997 | Bowie et al. |
| 5,712,096 A | 1/1998 | Stern et al. |
| 6,020,141 A | 2/2000 | Pontoliano et al. |
| 6,036,920 A | 3/2000 | Pantoliano et al. |
| 6,214,293 B1 | 4/2001 | Pantoliano et al. |
| 6,232,085 B1 | 5/2001 | Pantoliano et al. .......... 435/7.1 |
| 6,331,392 B1 | 12/2001 | Laing et al. |

FOREIGN PATENT DOCUMENTS

| | | |
|---|---|---|
| WO | WO 97/09342 | 3/1997 |
| WO | WO 97/42500 | 11/1997 |
| WO | WO 98/39484 | 9/1998 |

OTHER PUBLICATIONS

Rosengart et al., Biochem. Biophys. Res. Commun., 152:432–440 (1988).
Chavan et al., Biochemistry, 33:7193 (1994).
Airas, Biochem. Biophys. Acta, 425:193–200 (1976).
Wang, J. Biol. Chem., 268:20785–20790 (1993).
Grimaldi et al., Biochemistry, 21:145–151 (1982).
Zahnley. J. Inorganic Biochem., 15:67–78 (1976).
Doyle et al., Carbohydrate Res., 46:111–118 (1976).
Feng and Slinger, Biochemistry, 30:10150–10155 (1991).
Kahn, Biochemistry, 31:8829–8834 (1992).
Fernandez–Ballester et al., Biochem. J., 228:421–426 (1992).
Expert Report of James R. Broach on Issue of Patent Invalidity, Scriptgen Pharmaceuticals v. 3–Dimentional Pharmaceuticals, U.S. District Court, Delaware, Jan. 7, 2000.
Opening Brief in Support of Defendant's Motion for Summary Judgment on Invalidity, Scriptgen pharmaceuticals v. 3–Dimentional pharmaceuticals, U.S. District Court, Delaware, Jan. 7, 2000.
Scriptgen Pharmaceuticals, Inc.'s Answering Brief on Opposition to Defendant's Motion for Summary Judgment of Invalidity, Scriptgen Pharmaceuticals v. 3–Dimentional Pharmaceuticals, U.S. District Court, Delaware, Feb. 1, 2000.
Defendant's Reply Brief in Support of Defendant's Motion for Summary Judgment of Invalidity, Scriptgen Pharmaceuticals v. 3–Dimentional Pharmaceuticals, U.S. District Court, Delaware, Feb. 28, 2000.
Bowie, Identifying Determinants of Folding and Activity for a Protein of Unknown Structure, B.A., Chemistry, Carleton College (1981), Submitted to the Department of Biology if Partial Fulfillment of the Requirements fo the Degree of Doctor of Philosophy at the Massachusetts Institute of Technology, May 1989.
Enna, "Radioligand Binding Assays", Principals and Methods in Receptor Binding, pp. 13–33, Plenum Publishing Corp. (1987).
Fuller and Steranka, "Drug Discovery at the Enzyme level", Drug Discovery and Development, pp. 177–198, Humana Press (1987).
Enna, "Biochemical Approaches for Evaluating Drug–Receptor Interactions", Drug Discovery and Development, pp. 151–176, Humana Press (1987).
Baldwin, "Drug Design", Drug Discovery and Development, pp. 33–71, Humana Press (1987).
Williams and Malick, "Drug Discovery and Development", Drug Discovery and Development, pp. 3–29 (1987).
Kinner, "Receptor Binding as a Method for Drug Discovery", Drug Discovery and Development, Humana Press (1987).
Beith et al., Biochemical Medicine, 11:350–357 (1974).
Gething and Sambrook, Nature, 355:33–45 (1992).
Hardy and Randall, Science, 251:439–443 (1991).
Crotheres, D.M., Draft Opinion, Scriptgen Pharmaceuticals v. 3–Dimentional Pharmaceuticals, U.S. District Court, Delaware, pp. 1–15, Oct. 20, 1999.
Horwitz et al., Memorandum Opinion, Scriptgen Pharmceuticals v. 3–Dimentinal Pharmaceuticals, U.S. District Court, Delaware, Dec. 15, 1999.
Chen et al., Anal Chem. 64:3018–3023 (1992).
Silverman et al., Current Opinion in Chemical and Biochemistry, 397–403 (1998).
Volkin et al., "The Effect of Polyanions on the Stabilization of Acidic Fibroblast Growth Factor", Harnessing Biotechnology for the 22st Century, $9^{th}$ Int'l Biotechnology Symposium, American Chemical Society, pp. 298–302 Aug. 1992.
Pakula, "A genetic and Biological Analysis of the Bacteriophage .lamda. Cro Protein ", B.S., Biol. And Chem., Tufts Univ. (1980), Submitted to the Department of Biology in Partial Fulfillment of the Requirements for the Degree of Doctor of Philosophy at Massachusetts Institute of Technology, Sep. 1988.
Pantolliano, M.W., Senior Director, Biophysical Chemistry, 3–Dimentional Pharmaceuticals, Inc., "The ThermoFlou.RTM. Strategy for High–Throughput Screening of Chemical Libraries Against Therapeutic Targets Including Those Derived from Genomics", pp. 1–17 (1999).
Alderman, E.M., Director, Pharmaceutical Research, New Ventures, Zymark Corporation, "Abbreviating the Assay Development Process Through Sealable Automation Tehcnology" (1999).
Wainer, I.W., Professor of Pharmacology, Georgetown University of Medical Center, Immobilized Receptor–Based Liquid Chromotographic Stationary Phases for Rapid On–Line Screening (1999).
Little, J.N., Senior Vice President, Cetec Corporation, "A Powerful New Screening Technology Utilizing Capillary Electrophoresis" (1997).
Yeh, Li–An, Director, Drug Discovery, NEN Life Science Products, Development of a Novel Phospholipase C Assay in HTS: A Functional Assay for GPCR (1997).
Zhang et al., Analytical Biochemistry, 264:22–25 (1988).
Scott and Smith Science, 249:386–390 (1997).
Schellman, Biophysical Chemistry, 45:273–279 (1993).
Ferst, Current Opinion in Structural Biology, 7:3–9 (1997).
Brandts et al., American Laboratory, 22:30–4 (1990).
Brandts et al., Biochemistry, 29:6927–6940 (1990).
Barcelo et al., Chem. Biol. Interactions, 74:315–324 (1990).
Schellman, Biopolymers, 14:999–1019 (1975).
Weber et al., J. Am. Chem. Soc., 116:1717–1724 (1994).

Bouvier and Wiley, Science, 265:398–402 (1994).
Morton et al., Biochemistry, 34:8564–8575 (1995).
Volkin et al., Biochemistry, 34:8564–8575 (1995).
Pakula, Annu. Rev. Genet. 23:289–310 (1989).
Moos et al., Chapter 33, Annual Reports in Medicinal Chemistry (1993).
Gordon et al., Journal of Medicinal Chemistry, Applications of Combinatorial Technologies to Drug Discovery. 2. Combinatorial Organic Synthesis, Library Screening Strategies, and Future Directions, vol. 3, No. 10 (1994).
Gallop et al., Journal of Medicinal Chemistry, Applications of Combinatorial Technologis to Drug Discovery. 1. Background and Peptide Combinatorial Libraries, vol. 37, No. 9 (1994).
Devlin, Science, vol. 245 (1990).
Pace and Grimsley, Ribonuclease T.sub.1 is Stabilized by Cation and Anion Binding, American Chemical Society (1998).
Weber et al., Journal of American Chemical Society, vol. 116 (1994).
Walz, et al., The Journal of biological Chemistry, (1990).
Lam et al., Nature, vol. 354 (1991).
Pace, Archives of Biochemistry and Biophysics, 199:270–276 (1980).
Tsai et al., Pharmaceutical Research, vol. 10, No. 5 (1993).
Morton et al., Biochemistry, 34:8513 (1995).
Erikson et al., Nature, 335:371 (1992).
Derwent Publications. Abstract No. 75–43214W (1992).
Eftink, Biophys. J., 66:482–501 (1994).
Grant et al., Biochemistry, 31:9491–9501 (1992).
Lee et al., FEBS Letters, 339:165–167 (1994).
Harrington, Int. J. Biochem. 24:275–280 (1992).
Davidson et al., Proc. Natl. Acad. Sci. USA, 91:2146–2150 (1994).
Scott et al., Science, 249:386 (1990).
Weber et al., J. Am. Chem. Soc., 16: 2717 (1994).
Schellman, Biophysical Chem., 45:273 (1993).
Barcelo et al., Chem. Biol. Interactions, 74:315 (1990).
Nilsson et al., Annu. Rev. Microbiol., 45:607–635 (1991).
Merabet et al., Biochim. Biophys. Acta, 1161:272–278 (1993).
Baumann et al., Eur. J. Biochem., 170:267–272 (1987).
Draper et al., Meth. Enzymol., 259:281–305 (1995).
Gassen, Prog. Nuc. Acid Res. And Molec. Bio., 24:57–83 (1980).
Stanford et al., Nuc. Acid Res., 16:10643–10655 (1988).
Zapp et al., Anal. Biochem., 74:969–978 (1993).
Matthews et al., Anal. Biochem., 169:1–25 (1988).
Totsuka et al., BBRC, 208(I):168–173 (Mar. 8, 1995).
Kutyavin et al., Biochemistry, 35:1170–1176 (1996).
Woo et al., Nuc. Acid Res., 24:2470–2475 (1996).
Wang et al., Biochemistry, 35:12338–12346 (1996).
Wang et al., Biochemistry, 36:768–779 (1997).
Schwille et al., Biochemistry, 35:10182–10195 (1996).
Green et al., J. Mol. Biol., 235:237–246 (1994).
Lacowicz, Principles of Fluorescence Spectroscopy, pp. 111–115, Plenum Press (1983).
Introduction to Fluorescence Polarization, Fluorescence Polarization Hand Book: Methods in Fluorescence Polarization, Pan Vera Corp., Madison, WI (608)233–5050 (1996).

SCREEN EMPLOYING FLUORESCENCE ANISOTROPY TO IDENTIFY COMPOUNDS WITH AFFINITY FOR NUCLEIC ACIDS

This is a continuation, of application Ser. No. 09/060,449, filed Mar. 5, 1998, U.S. Pat. No. 6,331,392, which claims priority pursuant to 35 U.S.C. §119 from Provisional Application Ser. No. 60/039,911, filed Mar. 5, 1997. Each of these prior applications is hereby incorporated herein by reference, in its entirety.

FIELD OF INVENTON

This invention pertains to novel methods for screening for pharmaceutical compounds, in particular those that bind to RNA sequences involved in the pathogenesis of disease or in regulation of a physiological function.

BACKGROUND OF THE INVENTION

Pharmaceuticals can be developed from lead compounds that are identified through a random screening process directed towards a target, such as a nucleic acid or a protein receptor. Large scale screening approaches can be complicated by a number of factors. First, many assays are laborious or expensive to perform. Assays may involve experimental animals, cell lines, or tissue cultures that are difficult or expensive to acquire or maintain. These considerations often place practical limitations on the number of compounds that reasonably can be screened. Thus, those employing random screening methods are frequently forced to limit their search to those compounds for which some prior knowledge suggests that the compounds are likely to be effective. This strategy limits the range of compounds tested, and many useful drugs may be overlooked.

Furthermore, the specificity of many biochemical assays may exclude a wide variety of useful chemical compounds, because the interactions between the ligand and the target are outside the scope of the assay. With such a specific assay, many potential pharmaceuticals may not be detected.

Finally, in most existing biochemical screening approaches to drug discovery, the system in question must be well-characterized before screening can begin. Consequently, biochemical screening for therapeutic drugs directed against many targets must await detailed biochemical characterization, a process that generally requires extensive research.

The present invention pertains specifically to the use of RNA targets in high-throughput screening methods for identification of useful ligands. The invention takes advantage of the existence of higher-order structures in naturally-occurring and synthetic RNA molecules. For example, RNA exists in both single stranded and helical duplex forms. These duplexes may be distorted by loops, bulges, base triples and junctions between helices. The structural diversity of RNA is far greater than that of DNA, and similar to that of proteins, making RNA a likely target for unique binding of small molecules (reviewed in Wyatt and Tinoco, 1993).

Small molecules can bind RNA with high affinity and specificity and can block essential functions of the bound RNA. The best example of such molecules are antibiotics such as erythromycin and aminoglycosides. The first suggestion that some antibiotic translation inhibitors interact specifically with RNA was the genetic mapping of resistance to kanamycin and gentamicin to the methylation of 16S RNA (Thompson et al., *Mol. Gen. Genet.* 201:168, 1985). Erythromycin binds to bacterial RNA and releases peptidyl-tRNA and mRNA (Menninger et al., *Mol. Gen. Genet.* 243:225, 1994). 2-DOS-containing aminoglycosides bind specifically to the structures of HIV RNA known as the RRE, block binding of the HIV Rev protein to this RNA, and thereby inhibit HIV replication in tissue culture cells (Zapp et al., *Cell* 74:969, 1993). In addition, although aminoglycosides have long been developed as translation inhibitors, they were only recently shown to bind to rRNA in the absence of proteins (Purohit and Stern, *Nature* 370:659, 1994; Fourmy et al., *Science* 274:1367, 1996). Hygromycin B inhibits coronaviral RNA synthesis and is thought to do so by binding to the viral RNA and blocking specifically the translation of viral RNA (Macintyre et al., *Antimicrob. Agents Chemother.* 35:2630, 1991).

Existing assays for ligands of nucleic acids, such as, for example, methods that use equilibrium dialysis, differential scanning calorimetry, viscometric analyses, UV measurement of hyperchromic effect, or fluorescence, are often unfeasible for high-throughput applications, because of insufficient characterization, unavailability of components, expense, and/or complexity. (See, for example, Murakami et al., *Nuc.Acids Res.* 19:4097, 1991; Walker et al., *Nuc.Acids Res.* 24:348, 1996). Thus, prior to the present invention, random screening approaches for non-oligonucleotide ligands of RNA were limited to compounds for which some prior knowledge suggested that they might be effective. This strategy has been successful (Zapp et al., 1993), but is limited in the range of compounds that can be tested on a practical scale.

U.S. Pat. No. 5,270,163 describes the SELEX system for the identification of oligonucleotides that bind specific targets. In this system, random oligonucleotides are affinity-selected and amplified, followed by several cycles of reselection and amplification. This method, however, is limited to screening for oligonucleotide ligands and cannot be applied in reverse, i.e., to search for non-oligonucleotide ligands that bind to nucleic acids.

U.S. Pat. No. 5,306,619 discloses a screening method to identify compounds that bind particular DNA target sequences. In this method, a test nucleic acid is constructed in which the target sequence is placed adjacent to a known protein-binding DNA sequence. The effect of test compounds on the binding of the cognate protein to the protein-binding DNA sequence is then measured. This method requires conditions in which melting of DNA hybrids and unfolding of DNA structure do not occur. RNA, by contrast, can undergo much more dramatic variations in patterns of base-pairing and overall conformation.

Thus, there is a need in the art for efficient and cost-effective high-throughput methods for random screening of large numbers of non-oligonucleotide small molecules for their ability to bind physiologically, medically, or commercially significant RNA molecules.

SUMMARY OF THE INVENTION

The present invention encompasses screening methods to identify ligands that bind any predetermined target RNA. The methods are carried out by the steps of: selecting as test ligands a plurality of compounds not known to bind to the target RNA sequence; incubating the target RNA sequence with one or more fluorescently labeled probes in the presence of a test ligand to produce a test combination, and in the absence of a test ligand to produce a control combination; measuring one or more fluorescence properties of the probe(s) to evaluate the stability and/or conformation of the target RNA in each combination; and selecting as a ligand any test ligand that causes a measurable change in at least one of the fluorescence properties of the probes in the test combination relative to the control combination. Preferably, the incubating and measuring steps are repeated with a plurality of said test ligands until a ligand that binds to the target RNA sequence is identified. Furthermore, the test and control combinations may be subjected to conditions that, in the absence of ligands (i.e., in the control combination), denature a detectable fraction of the target RNA.

In general, ligands identified by the methods of the present invention are expected to stabilize, i.e., reduce $\Delta G°$ of a particular conformation of the target RNA. Stabilization may lead to a more folded conformation, a less folded conformation, or a change from a first folded conformation to a second, alternative, folded conformation. Preferably, ligands stabilize a particular conformation which inhibits the normal function of the target RNA.

Probes useful in practicing the invention include molecules which comprise fluorescent moieties whose measurable fluoresence properties, particularly polarization or anisotropy, are sensitive to the stability and/or conformation of the target RNA as reflected in the binding state of the probe. Preferably, the fluorescence anisotropy of a sample containing the probe is compared between the test and control combinations. Ligands may be identified as compounds that cause the anisotropy to increase or decrease relative to the anisotropy of a control solution.

In a preferred embodiment, the target RNA is hybridized with a complementary oligonucleotide to which one or more fluorescent probes have been attached, and the effect of test compounds on fluorescence anisotropy of the probe is used to detect ligand binding to the target RNA.

A "measurable change" in target RNA stability or conformation as detected by any of the above or other methods is one in which the difference in the measured parameter between the test and control combinations is greater than that expected due to random statistical variation.

DETAILED DESCRIPTION OF THE INVENTION

All patent applications, patents, and literature references cited in this specification are hereby incorporated by reference in their entirety. In case of conflict, the present description, including definitions, will prevail.

Definitions

As used herein, the term "ligand" refers to an agent that binds a target RNA. The agent may bind the target RNA when the target RNA is in a native or alternative conformation, or when it is partially or totally unfolded or denatured. According to the present invention, a ligand can be an agent that binds at any site on the target RNA. Therefore, the ligands of the present invention encompass agents that in and of themselves may have no apparent biological function, beyond their ability to bind to the target RNA.

As used herein, the term "test ligand" refers to an agent, comprising a compound, molecule or complex, which is being tested for its ability to bind to a target RNA. Test ligands can be virtually any agent, including without limitation metals, peptides, proteins, lipids, polysaccharides, small organic molecules, nucleotides (including non-naturally occurring ones) and combinations thereof. Typically, small organic molecules have a molecular weight of more than 50 yet less than about 2,500 daltons, and most preferably less than about 600 daltons. Preferably, test ligands are not oligonucleotides. Complex mixtures of substances such as natural product extracts, which may include more than one test ligand, can also be tested, and the component (or multiple component) that may bind the target RNA can be identifed and purified from the mixture in a subsequent step.

Test ligands may be derived from large libraries of synthetic or natural compounds. For example, synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Alternatively, libraries of natural compounds in the form of bacterial, fungal, plant and animal extracts are available from Pan Labs (Bothell, Wash.) or MycoSearch (NC), or are readily producible. Additionally, natural and synthetically produced libraries and compounds are readily modified through conventional chemical, physical, and biochemical means. For example, the compounds may be modified to enhance efficacy, stability, pharmaceutical compatibility, and the like. For example, once a peptide ligand has been identified using the present invention, it may be modified in a variety of ways to enhance its stability, such as using an unnatural amino acid, such as a D-amino acid, particularly D-alanine, or by functionalizing the amino or carboxyl terminus, e.g., for the amino group, acylation or alkylation, and for the carboxyl group, esterification or amidification, or through constraint of the peptide chain in a cyclic form, or through other strategies well known to those skilled in the art.

As used herein, the term "target RNA" refers to a RNA sequence for which identification of a ligand or binding partner is desired. Target RNAs include without limitation sequences known or believed to be involved in the etiology of a given disease, condition or pathophysiological state, or in the regulation of physiological function. Target RNAs may be derived from any living organism, such as a vertebrate, particularly a mammal and even more particularly a human, or from a plant, virus, bacterium, fungus, protozoan, parasite or bacteriophage. Target RNA may comprise wild type sequences, or, alternatively, mutant or variant sequences, including those with altered stability, activity, or other variant properties, or hybrid sequences to which heterologous sequences have been added. Furthermore, target RNA as used herein includes RNA that has been chemically modified, such as, for example, by conjugation of biotin, peptides, fluorescent molecules, modified nucleotides, and the like.

Target RNA sequences for use in the present invention are typically between about 5 and about 500 nt, preferably between about 30 and about 100 nt, and most preferably about 50 nt. Target RNAs may be isolated from native sources, or, more preferably, are synthesized in vitro using conventional polymerase-directed cell-free systems such as those employing T7 RNA polymerase or SP6 RNA polymerase (Studier et al., *Meth.Enzymol.* 185:60 (1990).

As used herein, "test combination" refers to the combination of a test ligand, one or more probes, and a target RNA. "Control combination" refers to the combination of a target RNA with one or more probes in the absence of a test ligand.

As used herein, the "folded state" of a target RNA refers to a native (lowest Gibbs free energy state) conformation of the sequence in the absence of denaturing conditions. The folded state of an RNA encompasses both particular patterns of intramolecular base-pairing, as well as higher-order structures stabilized by covalent or non-covalent bonding. Without wishing to be bound by theory, it is believed that certain target RNAs may achieve one of several alternative folded states stabilized by the lowest Gibbs free energy state, depending upon experimental conditions (including buffer, temperature, presence of ligands, and the like).

As used herein, the "unfolded state" of a target RNA refers to a situation in which the RNA has been rendered partially or completely single-stranded relative to its folded state(s) or otherwise lacks elements of its structure that are present in its folded state. The term "unfolded state" as used herein encompasses partial or total denaturation and loss of structure.

As used herein, a "measurable change" in RNA stability or conformation refers to a quantity that is empirically determined and that will vary depending upon the method used to monitor RNA stability or conformation. The present invention encompasses any difference between the test and control combinations in any measurable physical parameter, where the difference is greater than expected due to random statistical variation.

As used herein, a "probe" is any molecule that is intrinsically fluorescent or to which a fluorescent moiety is attached, in which one or more fluorescence properties are sensitive to the stability and/or conformation of the target RNA and/or to the binding state of the probe. Suitable probe compounds include without limitation nucleic acids, particularly oligonucleotides; small RNA-binding molecules exemplified by 2-deoxystreptamine antibiotics, which bind the Rev-responsive element in HIV RNA, or other compounds that specifically recognize the major or minor groove of RNA; and proteins, and peptides derived therefrom, that recognize particular RNA sequences or conformations.

Oligonucleotide probes may comprise any purine- and pyrimidine-containing polymers, including without limitation DNA, RNA, protein-nucleic acid, or combinations thereof. Furthermore, oligonucleotide probes may be modified so as to modulate their affinity for the target RNA; this may be achieved, for example, by changing the length of the olignucleotide; by introducing mismatches between otherwise complementary sequences; by employing nucleotide analogues that engage in stronger or weaker base-pairing than the original nucleotide (Kutyavin et al., *Biochemistry* 35:11170, 1996; Woo et al., *Nuc.Acids Res.* 24:2470, 1996); and by other chemical modifications known in the art. Similarly, small molecule probes or peptide- or protein-derived probes may be chemically modified using methods well known in the art in order to change their affinity for the target RNA. Fluorescent moieties which may be attached to the probe molecules include without limitation: fluorescein, rhodamine, BODIPY™ compounds, and derivatives thereof (Molecular Probes, Eugene Oreg.). Methods for conjugating these moieties to nucleic acids, peptides, and small organic molecules are disclosed in Haugland, *Handbook of Fluorescent Probes,* 5th Ed. (Molecular Probes, Eugene Oreg., 1992).

The present invention encompasses screening methods, particularly high-throughput methods, for identifying a ligand that binds a target RNA. If the target RNA to which the test ligand binds is associated with or causative of a disease or condition, the ligand may be useful for diagnosing, preventing or treating the disease or condition or for regulating the expression of a gene. A ligand identified by the present method can also be one that is used in a purification or separation method, such as a method that results in purification or separation of the target RNA from a mixture. The present invention also relates to ligands identified by the present method and their therapeutic uses (for diagnostic, preventive or treatment purposes) and uses in purification and separation methods.

According to the present invention, a ligand for a target RNA is identified by its ability to influence the extent or pattern of intramolecular folding or the rate of folding or unfolding of the target RNA and, more specifically, the energetic stability (Gibbs free energy state) of the target RNA. If the test ligand binds to the target RNA, the relative amounts of stabilized target RNA, folded or unfolded target RNA, or one or another of multiple alternative folded states of the target RNA, or the rate of folding or unfolding of the target RNA in the presence of the test ligand will be different, i.e., higher or lower, than that observed in the absence of the test ligand. Thus, the present method encompasses incubating the target RNA with probe in the presence and absence of a test ligand. This is followed by analysis of the differential stability and/or folding of the target RNA, preferably using fluorescence polarization as an indicator.

An important feature of the present invention is that it may detect any compound that binds to any region of the target RNA, not only to discrete regions that are intimately involved in a biological activity or function. It is contemplated that multiple ligands may be used simultaneously on the same target RNA, and may bind cooperatively or independently. In practicing the present invention, the test ligand is combined with a target RNA, and the mixture is maintained under appropriate conditions and for a sufficient time to allow binding of the test ligand to the target RNA. Equilibrium or non-equilibrium conditions may be used. In general, the test ligand is present in molar excess relative to the target RNA. As discussed in more detail below, the target RNA can be in a soluble form, conjugated to a larger molecule in solution, or bound to a solid phase matrix. Preferably, the test solution contains monovalent and divalent ions and has a pH of about 7.5, and the incubation is conducted at temperatures between about 25° C. and 40° C. ("physiological" conditions).

The time necessary for binding of target RNA to ligand will vary depending on the test ligand, target RNA and other conditions used. Preferably, binding will occur instantaneously (e.g., essentially simultaneous with combination of test ligand and target RNA), while in others, the test ligand-target RNA combination can be maintained for a longer time e.g. up to 12–16 hours, before binding is measured. When many test ligands are employed, an incubation time is chosen that is sufficient for most RNA:ligand interactions, typically about one hour. The appropriate time will be readily determined by one skilled in the art.

Other experimental conditions that are optimized for each RNA target include pH, reaction temperature, salt concentration, valency, and composition, amount of RNA, reducing agent concentration and composition, and the inclusion of non-specific protein and/or nucleic acid in the assay. An important consideration when screening chemical or natural product libraries is the response of the assay to organic solvents (e.g., dimethyl sulfoxide, methanol or ethanol) commonly used to resuspend such materials. Accordingly, each RNA is tested in the presence of varying concentrations of each of these organic solvents. Finally, the assay may be particularly sensitive to certain types of compounds, in particular intercalating agents, that commonly appear in chemical and especially natural product libraries. These compounds can often have potent, but non-specific, inhibitory activity. Some of the buffer components and their concentrations will be specifically chosen in anticipation of this problem. For example, bovine serum albumin will react with radicals and minimize surface adsorption. The addition of non-specific DNA or RNA may also be necessary to minimize the effect of nucleic acid-reactive molecules (such as, for example, intercalating agents) that would otherwise score as "hits" in the assay.

Binding of a test ligand to the target RNA is assessed by comparing the stability (Gibbs free energy) and/or the absolute amount of folded or unfolded target RNA in the absence and presence of test ligand, or, alternatively, by determining the ratio of folded:unfolded target RNA or change in the folded state of the target RNA, or the rate of target RNA folding or unfolding, or differential stability, in the absence and presence of test ligand. If a test ligand binds the target RNA (i.e., if the test ligand is a ligand for the target RNA), there may be significantly more stabilized or more folded target RNA (and, thus, a higher ratio of more stable to less stable or of folded to unfolded target RNA) than is present in the absence of a test ligand. Alternatively, binding of the test ligand may result in significantly less stabilized or less folded target RNA than is present in the absence of a test ligand. Another possibility is that binding of the test ligand changes the pattern or stabilization properties of alternative RNA folded structures. Similarly, binding of the test ligand may cause the rate of target RNA folding or unfolding to change significantly or may change the rate of acquisition of an alternative structure.

In any case, determination of the absolute amounts or ratios of stabilized and non-stabilized or folded and unfolded target RNA may be carried out using probes which comprise one or more fluorescent moieties (see below). Any stability-sensitive and/or conformation-sensitive probe to which an appropriate fluorescence moiety can be attached may be used in practicing the invention. For example, an oligonucleotide can be designed so that it will hybridize to a particular RNA target only when the RNA is in an unfolded conformation or to single-stranded regions in an otherwise folded conformation. A protein, or a peptide or structural domain derived therefrom, can be isolated that binds to a particular RNA target only when the RNA is in a particular folded conformation. For example, antibodies (or antigen combining sites derived therefrom) may be used that recognize specific RNA sequences (and/or conformations of such sequences) (Deutscher et al., *Proc.Natl.Acad.Sci.USA* 85:3299, 1988); bind to double-stranded or single-stranded RNA in a sequence-independent manner (Schonborn et al., *Nuc.Acids Res.* 19:2993, 1991); or bind DNA:RNA hybrids specifically (Stumph et al., *Biochem.* 17:5791, 1978).

For the purposes of high-throughput screening, the experimental conditions are adjusted to achieve a threshold proportion of test ligands identified as "positive" compounds or ligands from among the total compounds screened. This threshold is set according to two criteria. First, the number of positive compounds should be manageable in practical terms. Second, the number of positive compounds should reflect ligands with an appreciable affinity and specificity towards the target RNA. A preferred threshold is achieved when 0.1% to 1% of the total test ligands are shown to be ligands of a given target RNA within a specified binding affinity range.

Detection of RNA Ligands Using Fluorescence Polarization/Anisotropy

Fluorescence polarization or anisotropy is a highly sensitive method for detecting RNA ligands according to the present invention. When fluorescent molecules are excited with plane polarized light, they emit a majority of light in the same polarized plane, provided that the molecule remains stationary during the lifetime of the excited state (4 nanoseconds in the case of fluorescein). However, if the molecule rotates or tumbles out of the plane of the exciting polarized light during the excited state, light is emitted in a different plane from that of the initial excitation. The degree to which the fluorescence emission vector moves from, e.g., a vertical to a horizontal plane is directly related to the mobility of the fluorescently labeled molecule. That is, if the fluorescently labeled molecules are large, they move very little and the emitted light remains highly polarized with respect to the excitation plane. By contrast, if the fluorescently labeled molecules are small, they rotate or tumble faster, and the resulting emitted light is depolarized relative to the excitation plane (Lackowicz, *Principles of Fluorescence Spectroscopy*, Plenum Press, NY, 1983; *Methods in Fluorescence Polarization*, Panvera Corp, Madison Wis.).

Fluorescence polarization is defined as:

$$P = \frac{Int_{parallel} - Int_{vertical}}{Int_{parallel} + Int_{vertical}}$$

where $Int_{parallel}$ is the intensity of emission light parallel to the excitation plane and $Int_{vertical}$ is the intensity of emission light perpendicular to the excitation plane. P is a dimensionless number (expressed as "polarization units" or "millipolariztion units (mP)) and has a maximum value of 0.5 for fluorescein.

Fluorescence anisotropy is related to polarization in the following way:

$$A = \frac{Int_{parallel} - Int_{vertical}}{Int_{parallel} + 2Int_{vertical}} \quad \text{and} \quad A = \frac{2P}{3 - P}$$

Polarization/anisotropy is related to the speed at which a fluorescently labeled molecule rotates, which, in turn, is related to the size (molecular volume) of the fluorescent entity. Thus, when a fluorescently labeled oligonucleotide probe, for example, binds to a target RNA, the molecular volume of the fluorescent entity increases, and the fluorescence polarization value of the sample will be higher. In this embodiment, hybridization of the probe to the target RNA is allowed to proceed in the absence and presence of test ligands (i.e., in control and test combinations, respectively), and fluorescence polarization measurements are used to quantify the level of hybridization in test and control combinations. Ligands are identified as those compounds that cause a depolarization of the test combination relative to the control combination.

Figure 1:
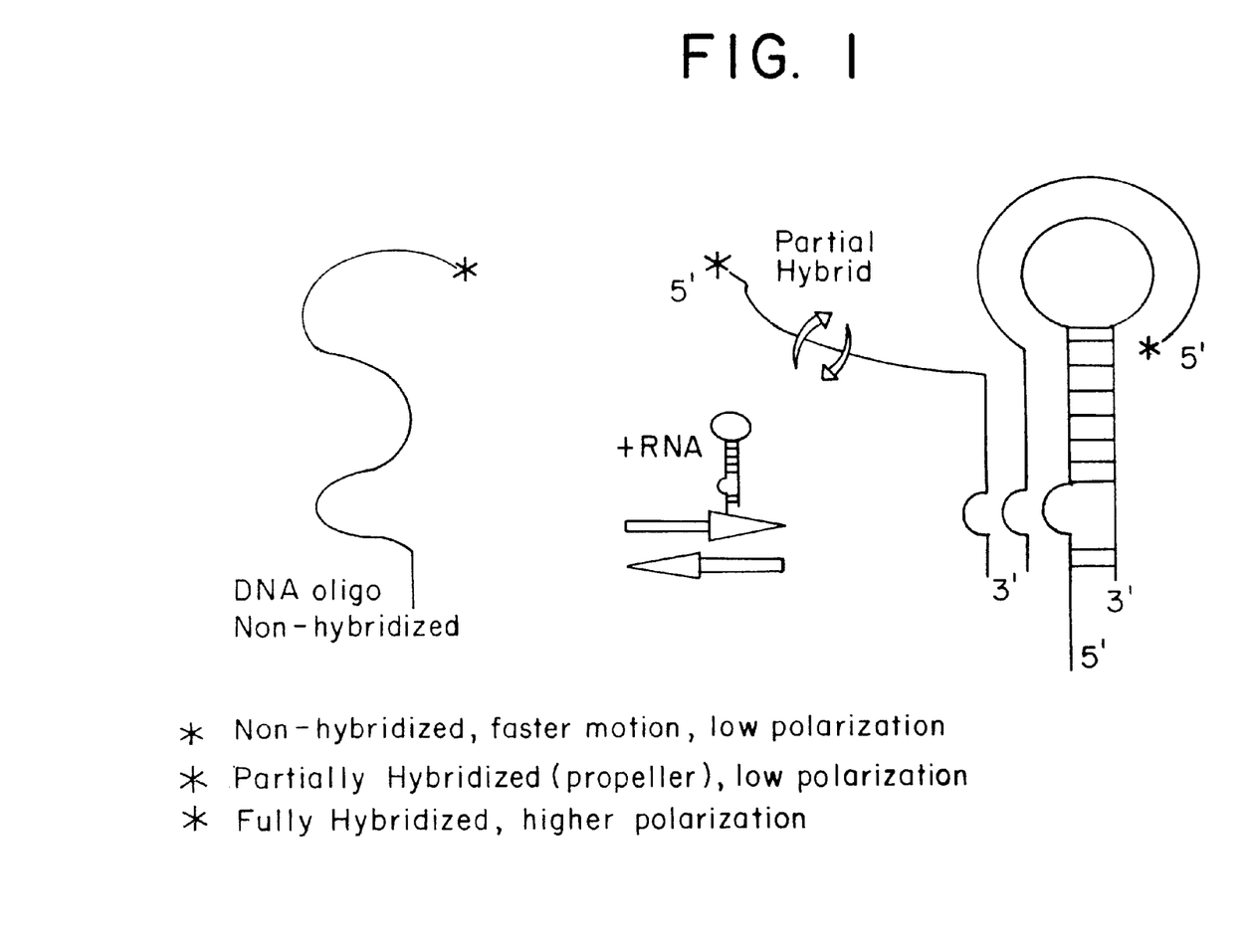
FIG. 1 is a schematic illustration of the equilibrium equation for the hybridization to a target RNA of a fluorophore attached to an oligonucleotide probe.
Figure 2:
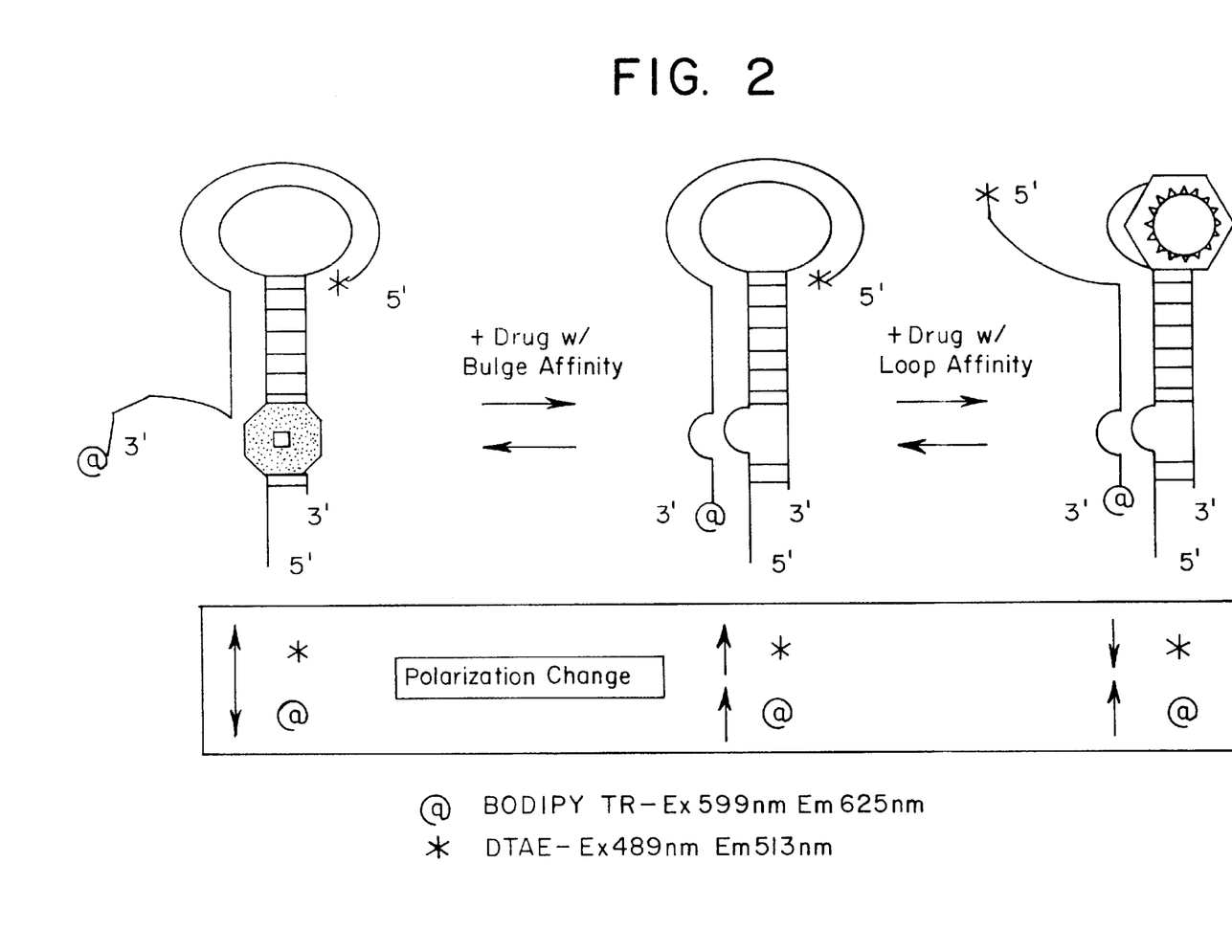
FIG. 2 is a schematic illustration of the effect on fluorescence polarization of a fluorophore binding to two different regions of a target RNA structure.
Figure 3:
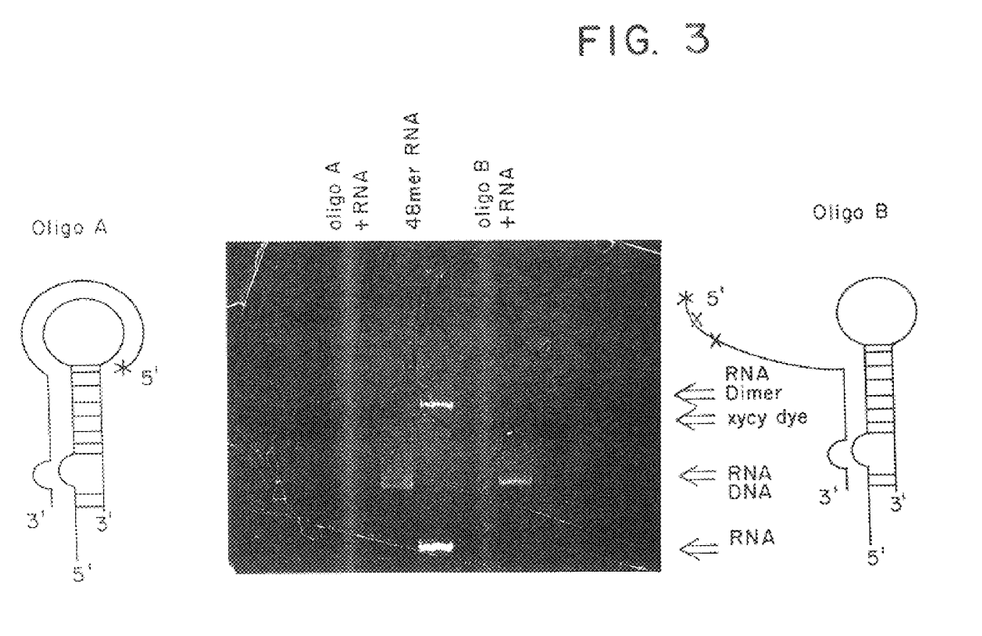
FIG. 3 shows a photograph of a 15% native polyacrylamide gel showing the formation of hybrids between a fluorescent probe and a target RNA.

The present invention encompasses the use of more than one fluorescent moiety attached to a single probe (see, e.g., FIG. 2), as well as the use of two or more probes (each having a different fluorophore) in a single reaction. In either case, the only requirement is that the different flurorescence properties of the different fluorophores should be such that their fluorescence polarization can in principle be measured simultaneously. This may be achieved, for example, by choosing fluorophores whose excitation and emission wavelength maxima do not significantly overlap.

The present invention is also particularly advantageous in allowing a direct determination of where in the target RNA the ligand binds. By individually conjugating a fluorophore to different regions of the probe molecule, it may be possible to ascertain what part of the target RNA structure is affected by ligand binding. Alternatively, multiple probes directed to different sites on the target RNA may be used.

Detection of ligands by measuring fluorescence polarization is particularly suitable for high-throughput applications. For example, two instruments exist that can measure polarization of samples present in 96-well microtiter dishes; these instruments are marketed by Panvera Corp (Madison Wis.) and Jolley Instruments (Chicago Ill.). Furthermore, the RNA target may be immobilized (either on beads or on the walls of the microtiter wells), or may be conjugated to a larger molecule in solution (such as, for example, to streptavidin via a biotin moiety attached to the target RNA), thereby enhancing differences in polarization of the fluorescent probe subsequent to ligand binding.

Applications

Binding to a given target RNA is a prerequisite for pharmaceuticals intended to modify directly the action of that RNA. Thus, if a test ligand is shown, through use of the present method, to bind an RNA that reflects or affects the etiology of a condition, it may indicate the potential ability of the test ligand to alter RNA function and to be an effective pharmaceutical or lead compound for the development of such a pharmaceutical. Alternatively, the ligand may serve as the basis for the construction of hybrid compounds containing an additional component that has the potential to alter the RNA's function. In this case, binding of the ligand to the target RNA serves to anchor or orient the additional component so as to effectuate its pharmaceutical effects.

The fact that the present method is based on physicochemical properties common to most RNAs gives it widespread application. The present invention can be applied to large-scale systematic high-throughput procedures that allow a cost-effective screening of many thousands of test ligands. Once a ligand has been identified by the methods of the present invention, it can be further analyzed in more detail using known methods specific to the particular target RNA used. For example, the ligand can be tested for binding to the target RNA directly, such as, for example, by using equilibrium dialysis or chromatographic frontal analysis. Furthermore, the ligand can be tested for its ability to influence, either positively or negatively, a known biological activity of the target RNA, such as (but not limited to) protein translation or RNA splicing.

Non-Limiting examples of RNA targets to which the present invention can be applied are shown in the following table:

| Therapeutic Area | RNA Targets |
|---|---|
| Antivirals | HBV epsilon sequence; HCV 5' untranslated region; HIV packaging sequence, RRE, TAR; picornavirus internal translation enhancer |
| Antibacterials | RNAse P, tRNA, rRNA (16S and 23S), 4.5S RNA |

-continued

| Therapeutic Area | RNA Targets |
|---|---|
| Antifungals | Similar RNA targets as for antibacterials, as well as snRNA |
| Rheumatoid Arthritis | Alternative splicing of CD23 |
| Cancer | Metastatic behavior is conferred by alternatively-spliced CD44; mRNAs encode proto-oncogenes; telomere length |
| CNS | RNA editing alters glutamate receptor-B, changing calcium ion permeability |
| Neurofibromatosis type I | RNA editing introduces stop codon at 5' end of NF1 GAP-related domain to inactivate NF1 epigenetically |
| Cardiovascular | RNA editing influences amount of ApoB-100, strongly associated with atherosclerosis |

The following example is intended to further illustrate the invention without limiting it thereof.

EXAMPLE 1

Use of Fluorescence Polarization to Identify RNA-Binding Ligands

Figure 4:
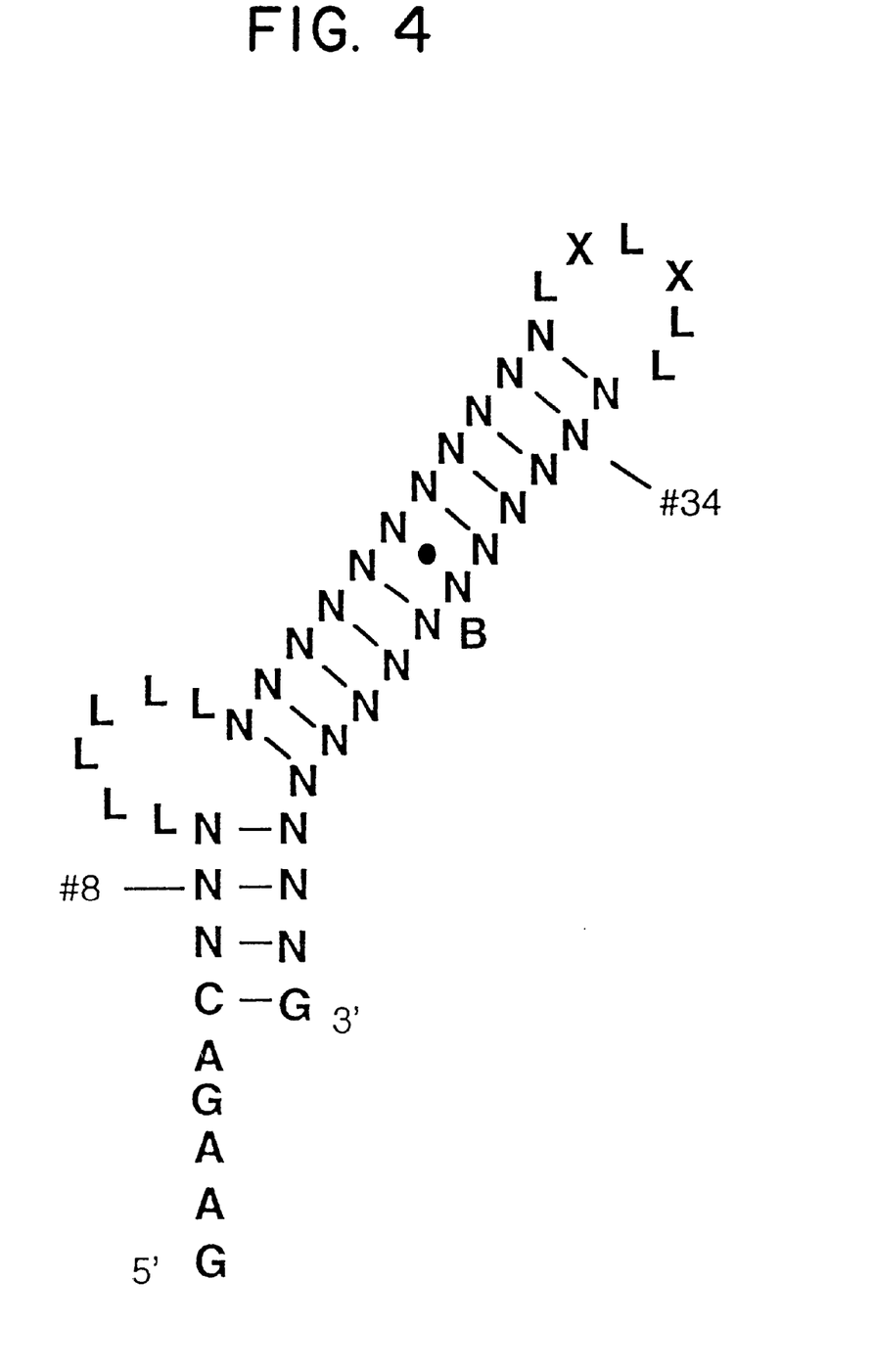
FIG. 4 is a schematic illustration of a model target RNA structure.

The following experiment was performed to demonstrate that measurements of fluorescence polarization can be used to discriminate different types of probe binding to target RNA. The target is a 48-nucleotide RNA that forms a stem-loop structure as shown in FIG. 4 (bottom), containing a large distal loop and a smaller proximal loop, also known as an assymetric bulge (see FIG. 4). The probes, designated Oligo A and Oligo B, are 27-nucleotide DNA molecules which hybridize to nucleotides 8–34 of the target RNA. Oligo A and Oligo B differ only in the region complementary to the distal loop; Oligo B has mismatches (Xs) in place of canonical Watson-Crick base pairing at two sites. The probes were fluorescently labeled at their 5' ends using BODIPY-Texas Red (Molecular Probes, Eugene Oreg.), using the manufacturer's recommended conditions.

Figure 5A:
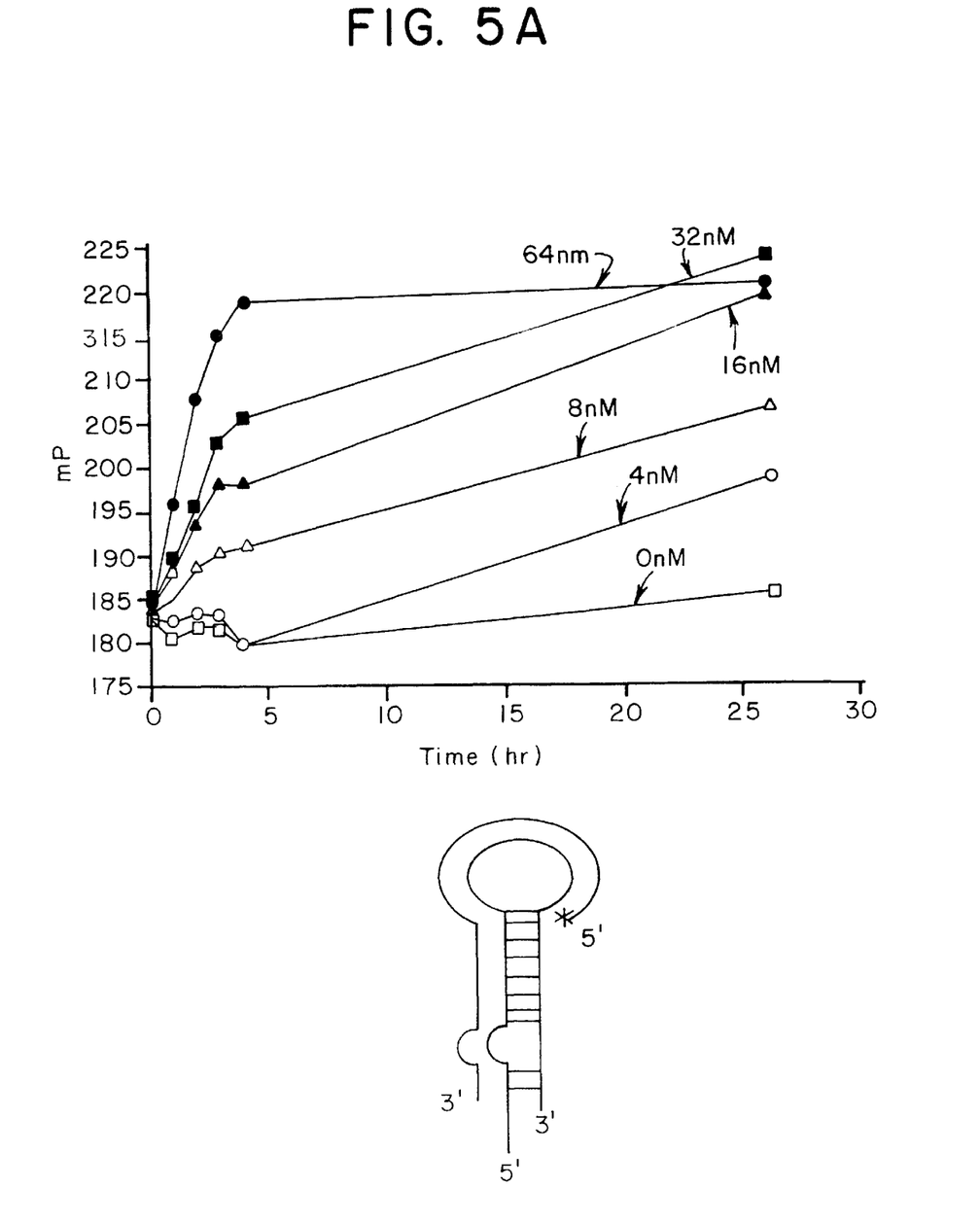
FIG. 5 is a graphic illustration of the time course of fluorescence polarization of hybridization reactions between the target RNA shown schematically in FIG. 4 and two different fluorescently-labeled oligonucleotide probes. mP, millipolarization units.
Figure 5B:
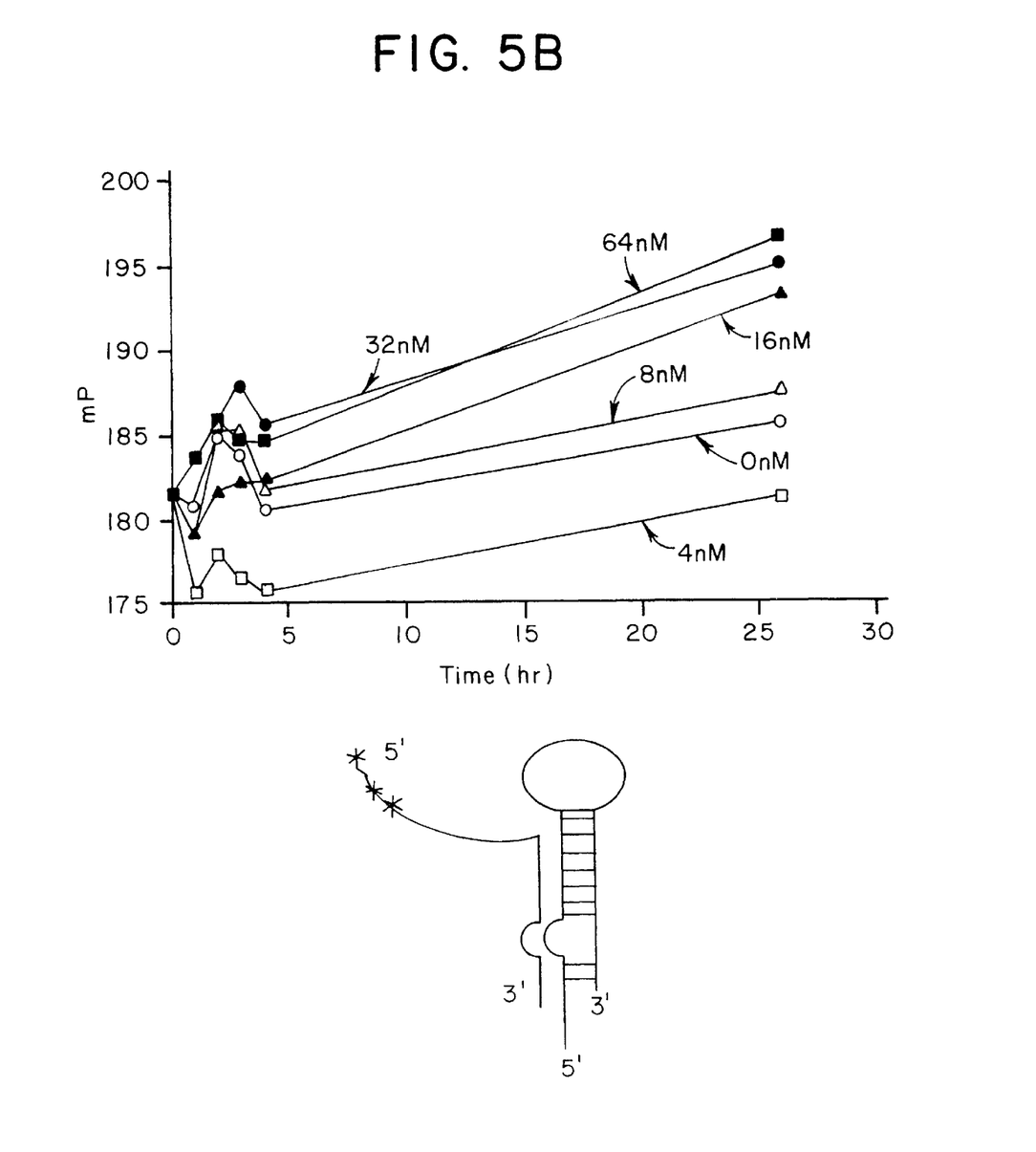

Reaction mixtures were set up containing: target RNA at concentrations ranging from 0–64 nM; and Oligo A or Oligo B at a concentration of 1 nM, in a solution of 50 mM Tris-HCl, pH 7.5, 150 mM KCl. The fluorescence polarization of each reaction was monitored at 25° C. for the indicated times (FIG. 5) using a Jolley Instruments FPM-1 fluorescence polarimeter (Chicago Ill.). The ordinate data are expressed as millipolarization units (mP).

The results (FIG. 5) indicate that Oligo A, which fully hybridizes to the target RNA, attains a higher polarization value than Oligo B, which does not fully hybridize (and in which the fluorescent moiety is presumably more free to rotate in solution). The reaction containing Oligo B is analogous to one in which a ligand binds to the target RNA at the distal loop, which would prevent the binding of a probe such as Oligo A.

Many variations of the present invention will suggest themselves to those skilled in the art in light of the above-detailed description. Such obvious variations are within the full intended scope of the appended claims.

What is claimed is:

1. A method for identifying a ligand that binds a predetermined target RNA sequence, which comprises:
    (a) selecting as test ligands a plurality of compounds not known to bind to the target RNA sequence;
    (b) incubating the target RNA sequence with one or more fluorescently labeled probes in the presence of a test ligand to produce a test combination;

(c) incubating the target RNA sequence with said one or more probes in the absence of a test ligand to produce a control combination;

(d) measuring one or more fluorescence properties of said probe; and (e) selecting as a ligand any test ligand that causes a measurable change in at least one of the fluorescence properties measured in step (d) in the test combination relative to the control combination, wherein said property reflects the stability and/or conformation of said target RNA.

2. A method as defined in claim 1, further comprising (a) repeating steps (b)–(e) with a plurality of said test ligands until a ligand that binds to the target RNA sequence is identified.

3. A method as defined in claim 1, wherein the fluorescence property measured in step (d) is fluorescence polarization.

4. A method as defined in claim 3, further comprising subjecting the test and control combinations to conditions that denature a detectable fraction of the target RNA sequence in the control combination.

5. A method as defined in claim 4, wherein the subjecting comprises at least one of altering the temperature, altering the salt concentration, adding denaturing compounds, and combinations thereof.

6. A method as defined in claim 3, wherein the target RNA is from about 5 to about 500 nucleotides in length.

7. A method as defined in claim 3, wherein the probe comprises an oligonucleotide that preferentially hybridizes to a predetermined conformation of the target RNA.

8. A method as defined in claim 3, wherein said probe comprises two or more different fluorescent moieties.

9. A method as defined in claim 3, wherein in step (b), said target RNA sequence is incubated with two or more different probes.

* * * * *